United States Patent

Pelerin

[11] Patent Number: 5,213,498
[45] Date of Patent: May 25, 1993

[54] METHOD FOR MAKING A CUSTOM IMPRESSION TRAY

[75] Inventor: Joseph Pelerin, Auburn Hills, Mich.

[73] Assignee: Advantage Dental Products, Inc., Auburn Hills, Mich.

[21] Appl. No.: 863,145

[22] Filed: Apr. 2, 1992

Related U.S. Application Data

[63] Continuation of Ser. No. 517,582, May 1, 1990.

[51] Int. Cl.⁵ .................................................. A61C 9/00
[52] U.S. Cl. ......................................... 433/37; 433/214; 433/48
[58] Field of Search ...................... 433/214, 41, 48, 37

[56] References Cited

U.S. PATENT DOCUMENTS

| | | | |
|---|---|---|---|
| 3,654,703 | 4/1972 | McAdoo | 433/48 |
| 4,227,877 | 10/1980 | Tureaud et al. | 433/37 |
| 4,413,979 | 11/1983 | Ginsburg et al. | 433/41 |
| 4,424,034 | 1/1984 | Korwin et al. | 433/41 X |
| 4,569,342 | 2/1986 | von Nostitz | 433/48 X |
| 4,657,509 | 4/1987 | Morris | 433/41 X |
| 4,668,188 | 5/1987 | Wolfenson et al. | 433/37 |
| 4,768,951 | 9/1988 | Abiru et al. | 433/37 X |
| 4,881,713 | 11/1989 | Wise | 433/48 X |
| 5,011,407 | 4/1991 | Pelerin | 433/48 |
| 5,026,278 | 6/1991 | Oxman et al. | 433/41 |
| 5,040,976 | 8/1991 | Ubel, III et al. | 433/41 |
| 5,066,231 | 11/1991 | Oxman et al. | 433/214 |

Primary Examiner—Gene Mancene
Assistant Examiner—Nicholas D. Lucchesi
Attorney, Agent, or Firm—Gifford, Groh, Sprinkle, Patmore and Anderson

[57] ABSTRACT

A method for making a custom impression tray is disclosed. The method includes the steps of heating a thermosetting material, such as polycaprolactone until the material becomes pliable and then molding the material in the area of the mouth for which a custom impression tray is desired. The material, upon cooling, sets thus forming a custom impression tray which is then removed from the mouth.

2 Claims, 1 Drawing Sheet

METHOD FOR MAKING A CUSTOM IMPRESSION TRAY

This is a continuation of copending application Ser. No. 07/517,582, filed on May 1, 1990, now abandoned.

BACKGROUND OF THE INVENTION

I. Field of the Invention

The present invention relates to a method for making a temporary crown or temporary laminate in dental applications.

II. Description of the Prior Art

It is frequently necessary to construct temporary crowns or onlays in dental applications, such as preparing caps for teeth. In such applications, the temporary crown protects the exposed tooth until a permanent crown can be fabricated and installed.

In the previously known method for constructing a temporary crown, the dentist utilizes an impression tray which is selected to cover the selected area or quadrant of the patient's mouth. This tray is typically filled with alginet or similar material and then placed in the patient's mouth in the affected area. After the alginet sets, the alignet forms a mold of the affected area of the patient's mouth.

Thereafter, the dentist uses the mold created by the alginet to create a temporary crown which is then cemented onto the tooth after the dentist has machined, ground or filed the tooth to the desired shape.

This previously known method for creating temporary crowns, however, suffers from several disadvantages. One such disadvantage is that the overall method for creating the temporary crown is detailed and time consuming. Consequently, the previously known method for creating temporary crowns requires extended "chair time" for the patient and dentist.

A still further disadvantage of this previously known method for creating temporary crowns is that the alignet or like material which is used to take an impression of the affected area of the mouth is relatively expensive. This, of course, increases the costs of making the temporary crown.

SUMMARY OF THE PRESENT INVENTION

The present invention provides a method for making a temporary crown or onlay which overcomes the above mentioned disadvantages of the previously known methods.

In brief, the method of the present invention comprises the steps of first heating a thermosetting material until the material becomes pliable. Preferably, the thermosetting material is polycaprolactone which becomes pliable at a temperature range of between 136° and 140° F. but is rigid at the temperature of the mouth, i.e. about 98° F.

The thermosetting material, while still pliable is then molded in the area of the mouth for which a temporary crown is desired. After the thermosetting material has cooled and set, it forms a temporary crown matrix which is then removed from the mouth. The dentist then grinds or otherwise shapes the tooth as required.

After the tooth is machined, an acrylic or other composite is then placed in the temporary crown matrix and the matrix is then pressed in the affected area of the mouth for which a temporary crown is desired. Upon hardening, the acrylic or other similar composite is then removed from the mouth together with the temporary crown matrix. The now hardened acrylic forms a temporary crown which is removed from the matrix and cemented in place on the tooth using temporary crown cement.

The method of the present invention can also be used for making a temporary facing matrix as well as other temporary laminates.

BRIEF DESCRIPTION OF THE DRAWING

A better understanding of the present invention will be had upon reference to the following detailed description, when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 1:
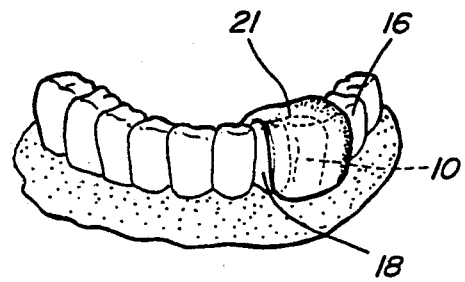
FIG. 1 is an elevational view illustrating the preferred method of the present invention.

With reference first to FIG. 1, the present invention discloses a method for constructing a temporary crown for a tooth 10 in a mouth. As is well known, when the tooth 10 is ground or filed in order to receive a cap, a temporary crown must be installed on top of the machined tooth to protect the tooth until a permanent crown or cap can be manufactured.

Figure 3:
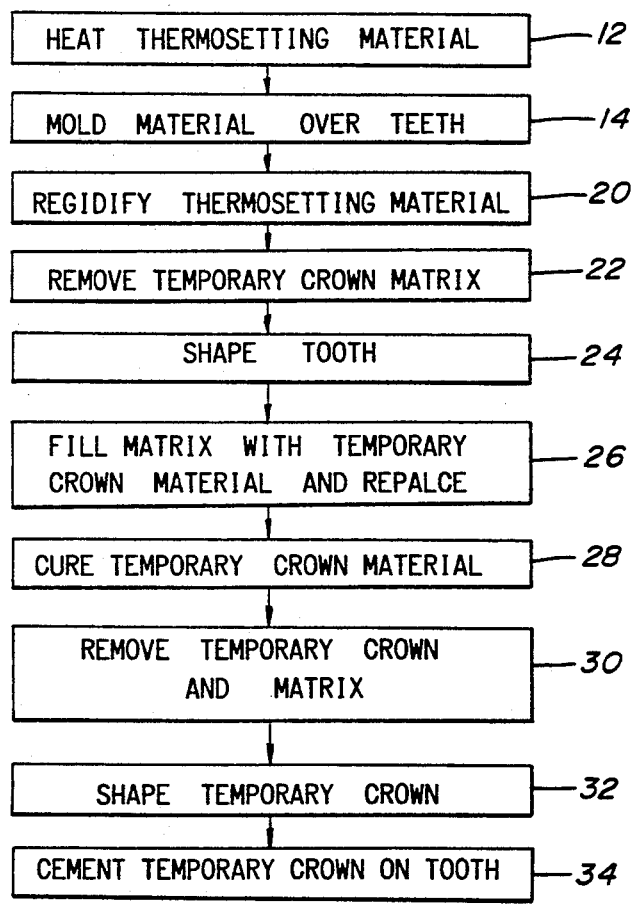
FIG. 3 is a flow chart illustrating the preferred method of the present invention.

With reference now to FIG. 3, the method of the present invention comprises a first step 12 of heating a thermosetting material to a predetermined temperature range at which the thermosetting material becomes pliable. In the preferred form of the invention, the thermosetting material is polycaprolactone which becomes pliable in a temperature range of between 136° and 140° F. Polycaprolactone, however, is rigid at mouth temperature, i.e. 98° F.

After the thermosetting material is pliable, the thermosetting material is molded at step 14 in the area of the mouth for which a temporary crown is desired. In this case, the material 14 is molded not only over the affected tooth 10 (FIG. 1) but also over the adjacent teeth 16 and 18.

Figure 2:
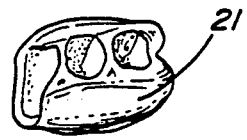
FIG. 2 is an elevational view of a preferred matrix.

At step 20, the thermosetting material is allowed to cool and set on the teeth 10, 16 and 18 until the thermosetting material becomes rigid. Once rigid, the thermosetting material forms a temporary crown matrix 21 (FIG. 2). Additionally, if desired, the thermosetting material can be sprayed with a coolant, such as water during step 20 in order to reduce the setting time for the thermosetting material.

The temporary crown matrix 21 is then removed at step 22. Once the temporary crown matrix 21 has been removed, the temporary crown matrix 21 forms a mold of the tooth 10 and portions of the adjacent teeth 16 and 18. The tooth 10 is then machined by grinding or filing in order to prepare the tooth 10 for receiving a crown. Shaping of the tooth 10 is done in any conventional fashion.

After the tooth 10 has been shaped at step 24, the temporary crown matrix 21 is first coated with a separating agent, such as petroleum or silicon jelly, and then filled with a temporary crown material, such as acrylic or composite. The temporary crown matrix 21 together with the temporary crown material is then repositioned in step 26 over the teeth 16, 10 and 18 and pressed down into the same position that the temporary crown matrix 21 had when it was formed at step 20.

With the matrix 21 filled with the temporary crown material repositioned across the teeth 10, 16 and 18 in step 26, the temporary crown material fills the space between the temporary crown matrix 21 and the tooth 10, i.e. the temporary crown material fills the space of the tooth material that was removed during the shaping step 24. Thus, the temporary crown material is molded at step 26 into the desired shape for the temporary crown.

At step 28, the temporary crown material is cured until it rigidifies. For some materials, the temporary crown material will cure after a predetermined period of time. However, since the thermosetting material is preferably either translucent or transparent, a light curable temporary crown material can alternatively be used. In this latter case the temporary crown material is cured by shining the light directly through the temporary crown matrix 21 onto the temporary crown material.

At step 30, after the temporary crown material has cured, the temporary crown matrix 21 together with the now cured temporary crown is removed from the mouth. The temporary crown is then removed from the matrix by simply popping the temporary crown out of the matrix 21. In practice, the separating agent facilitates removal of the temporary crown from the matrix.

At step 32 any excess temporary crown material, such as flashing, is trimmed from the temporary crown and the temporary crown is then cemented on the machined tooth 10 using temporary crown cement at step 34. The temporary crown matrix 21 is then preferably saved with the patient's record in case it is necessary to make a second temporary crown before the permanent crown is manufactured and installed.

Although the present invention has been previously described for constructing temporary crowns or onlays and/or bridge work, it can also be effectively used for making temporary facings and other temporary laminates. In this case, a temporary laminate material, such as light cure composite, is used in lieu of the temporary crown material. Other uses for the material include constructing a border molding lip for a denture impression tray as well as for marking bite registration. It also is less brittle and has more working time than current border mold materials.

Still other uses for the thermosetting material are applicable. One such use is to form a bite registration tray from the material. This is particularly useful in orthodontic applications, crown and bridge and removable partial denture procedures.

The thermosetting material can also be used to form a coping transfer impression. In this application, the thermosetting material, when pliable, is molded around a metal coping seated on the prepared tooth(s). The patient may occlude if desired. The material sets and is removed with the coping included and sent to a lab for final porcelain work.

The thermosetting material can also be used to take dental impressions by forming a custom impression tray. In this case the material, when pliable, is molded around the patient's teeth and/or edentulous gingiva, subjected to patient occlusion, allowed to cure or set, and then removed. This is particularly useful for obtaining impressions of broken teeth or preexisting dentitision since it is fast, inexpensive and replaces the previously used tray and alginet (or like impression material) procedure.

A temporary TMJ splint can also be formed from the thermosetting material. Similarly, the material can be used to stabilize traumatized teeth, such as loose teeth, by molding the material, when pliable, around the traumatized tooth and the adjacent teeth, and then allowing the material to set. This is much faster and easier than wiring or composite bonding currently used for this purpose.

The thermosetting material can also be molded, when pliable, to form a custom bleach tray for whitening teeth.

Figure 4:
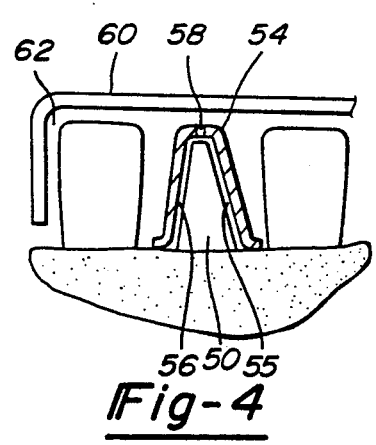
FIG. 4 is a view illustrating a method for a final impression coping.

With reference now to FIG. 4, a novel method for creating a highly accurate final impression for a crown or bridge is shown. As shown in FIG. 4, after a tooth 50 is shaped, the thermosetting impression material is molded around the shaped tooth and allowed to set. The resulting mold 54 is then coated with an adhesive 55, injected with a rubber impression material 56 such as polyvinylsiloxane, and then pressed over the shaped tooth 50 to the position shown in FIG. 4. An air vent 58 in the mold 54 insures that all air escapes as the mold is pressed over the shaped tooth. The air vent or hole may also be used to inject impression material.

A tray 60 filled with rubber impression material 62 is then pressed over the shaped tooth 50 and the adjacent teeth to form the final impression. In doing so, the mold 54 becomes imbedded in the impression material 62 in the tray 60 and is removed along with the final impression.

The thermosetting material can also be used to form a custom impression tray.

From the foregoing, it can be seen that the method of the present invention provides a simple, inexpensive and rapid method for making temporary crowns, facing laminates and the like in dental applications.

Having described my invention, however, many modifications thereto will become apparent to those skilled in the art to which it pertains without deviation from the spirit of the invention as defined by the scope of the appended claims.

I claim:
1. A method for making a custom impression tray for dental applications, comprising the steps of:
  (1) heating an original unidentified mass of thermosetting material to a predetermined temperature range at which the thermosetting material becomes pliable, said thermosetting material is polycaprolactone;
  (2) molding said mass of material while pliable in the area of the mouth or model of a mouth for which a custom impression tray is desired; and
  (3) allowing the thermosetting material to cool and set thereby forming a custom impression tray.

2. A method for making a custom impression tray for dental applications comprising the steps of:
  (1) heating an original unidentified mass of thermosetting material to a predetermined temperature range at which the thermosetting material becomes pliable, the material being polycaprolactone
  (2) molding said mass of material while pliable in the area of the mouth for which a custom impression tray is desired, and
  (3) after patient occulusion, allowing the thermosetting material to cool and set thereby forming a custom impression tray.

* * * * *

UNITED STATES PATENT AND TRADEMARK OFFICE
CERTIFICATE OF CORRECTION

PATENT NO. : 5,213,498

DATED : May 25, 1993

INVENTOR(S) : Joseph Pelerin

It is certified that error appears in the above-identified patent and that said Letters Patent is hereby corrected as shown below:

Column 1, line 25, delete "alignet" and insert --alginet--.
Column 1, line 39, delete "alignet" and insert --alginet--.
Column 4, line 63, after mouth insert -- or model of a mouth--.
Column 4, line 65, delete "after patient occlusion."

Signed and Sealed this

Thirty-first Day of May, 1994

BRUCE LEHMAN

Attest:

Attesting Officer

Commissioner of Patents and Trademarks